(12) United States Patent
Mikkola

(10) Patent No.: US 9,275,187 B2
(45) Date of Patent: Mar. 1, 2016

(54) PROGRAMMABLE TEST CHIP, SYSTEM AND METHOD FOR CHARACTERIZATION OF INTEGRATED CIRCUIT FABRICATION PROCESSES

(75) Inventor: Esko O. Mikkola, Tucson, AZ (US)

(73) Assignee: Ridgetop Group, Inc., Tucson, AZ (US)

( * ) Notice: Subject to any disclaimer, the term of this patent is extended or adjusted under 35 U.S.C. 154(b) by 1018 days.

(21) Appl. No.: 13/424,025

(22) Filed: Mar. 19, 2012

(65) Prior Publication Data

US 2012/0245879 A1    Sep. 27, 2012

Related U.S. Application Data

(60) Provisional application No. 61/465,463, filed on Mar. 21, 2011.

(51) Int. Cl.
| | |
|---|---|
| G06F 17/50 | (2006.01) |
| G06F 11/22 | (2006.01) |
| G06F 11/00 | (2006.01) |
| G01R 31/28 | (2006.01) |
| G06F 19/00 | (2011.01) |
| H01L 21/66 | (2006.01) |

(52) U.S. Cl.
CPC ............ *G06F 19/00* (2013.01); *G01R 31/2884* (2013.01); *H01L 22/34* (2013.01); *B01L 2300/0825* (2013.01); *G06F 19/3418* (2013.01)

(58) Field of Classification Search
CPC . B01L 2300/0825; G06F 17/00; G06F 19/00; G06F 19/3481; G01R 31/2884; H01L 22/34
USPC .......................... 716/51, 136; 714/25, 30, 733
See application file for complete search history.

(56) References Cited

U.S. PATENT DOCUMENTS

| | | | | | |
|---|---|---|---|---|---|
| 4,620,282 | A | * | 10/1986 | Shelley | ........................... 324/66 |
| 4,907,230 | A | * | 3/1990 | Heller et al. | .................. 714/724 |
| 5,778,004 | A | * | 7/1998 | Jennion | ............ G01R 31/31903 |
| | | | | | 714/724 |
| 6,052,197 | A | * | 4/2000 | Drake | .......................... 356/445 |
| 6,218,205 | B1 | * | 4/2001 | Michalicek | ..................... 438/28 |
| 7,239,163 | B1 | * | 7/2007 | Ralston-Good et al. | ... 324/750.3 |
| 7,271,608 | B1 | * | 9/2007 | Vermeire et al. | ........... 324/750.3 |
| 7,366,939 | B2 | * | 4/2008 | Le et al. | ........................ 713/400 |
| 7,437,589 | B2 | * | 10/2008 | Le et al. | ........................ 713/400 |
| 7,496,466 | B2 | * | 2/2009 | Farkas | ......................... 702/117 |
| 7,501,832 | B2 | * | 3/2009 | Spuhler et al. | ................ 324/537 |
| 7,519,886 | B2 | * | 4/2009 | Tsao | .............. G01R 31/318555 |
| | | | | | 365/201 |

(Continued)

OTHER PUBLICATIONS

Keane et al., "An Array-Based Test Circuit for Fully Automated Gate Dielectric Breakdown Characterization," IEEE 2008 Custom intergrated Circuits Conference (CICC), pp. 121-124.

(Continued)

*Primary Examiner* — Helen Rossoshek
(74) *Attorney, Agent, or Firm* — Eric A. Gifford

(57) ABSTRACT

A test chip, system and method for testing large numbers of test devices on a single test chip decreases the time and complexity required to characterize the variation and reliability of the IC fabrication process. A remotely configurable test chip can be programmed with varying bias conditions for testing of process variation or numerous failure modes on large sample sizes. An on-chip addressing technique allows large numbers of test devices to be tested simultaneously and the measurement signals read out serially for different test devices. The test chip may be configured for wafer, die or package-level testing.

19 Claims, 18 Drawing Sheets

(56) References Cited

U.S. PATENT DOCUMENTS

| | | | |
|---|---|---|---|
| 7,673,197 B2 * | 3/2010 | Luff et al. | 714/724 |
| 7,797,578 B2 * | 9/2010 | Co | G11C 29/56 714/25 |
| 7,979,225 B2 * | 7/2011 | Muller et al. | 702/82 |
| 8,937,482 B1 * | 1/2015 | Lemczyk | 324/750.05 |
| 2005/0193306 A1 * | 9/2005 | Luff et al. | 714/746 |
| 2007/0241068 A1 * | 10/2007 | Pamula et al. | 210/806 |
| 2014/0156253 A1 * | 6/2014 | McIlvain | G06F 11/27 703/28 |

OTHER PUBLICATIONS

Argawal et al., "A Test Structure for Characterizing Loca Device Mismatches," 2006 Symposium on VLSI Circuits Digest of Technical Papers, IEEE.

Pang et al, "Impact of Layout on 90nm CMOS Process Parameter Fluctuations," 2006 Symposium on VLSI Circuits Digest of Technical Papers, IEEE.

Kim et al., "Silicon Odometer: An On-Chip Reliability Monitor for Measuring Frequency Degradation of Digital Circuits," IEEE Journal of Solid-State Circuits, vol. 43, No. 4, Apr. 2008, http://hdl.handle.net/10220/6327, pp. 874-880.

* cited by examiner

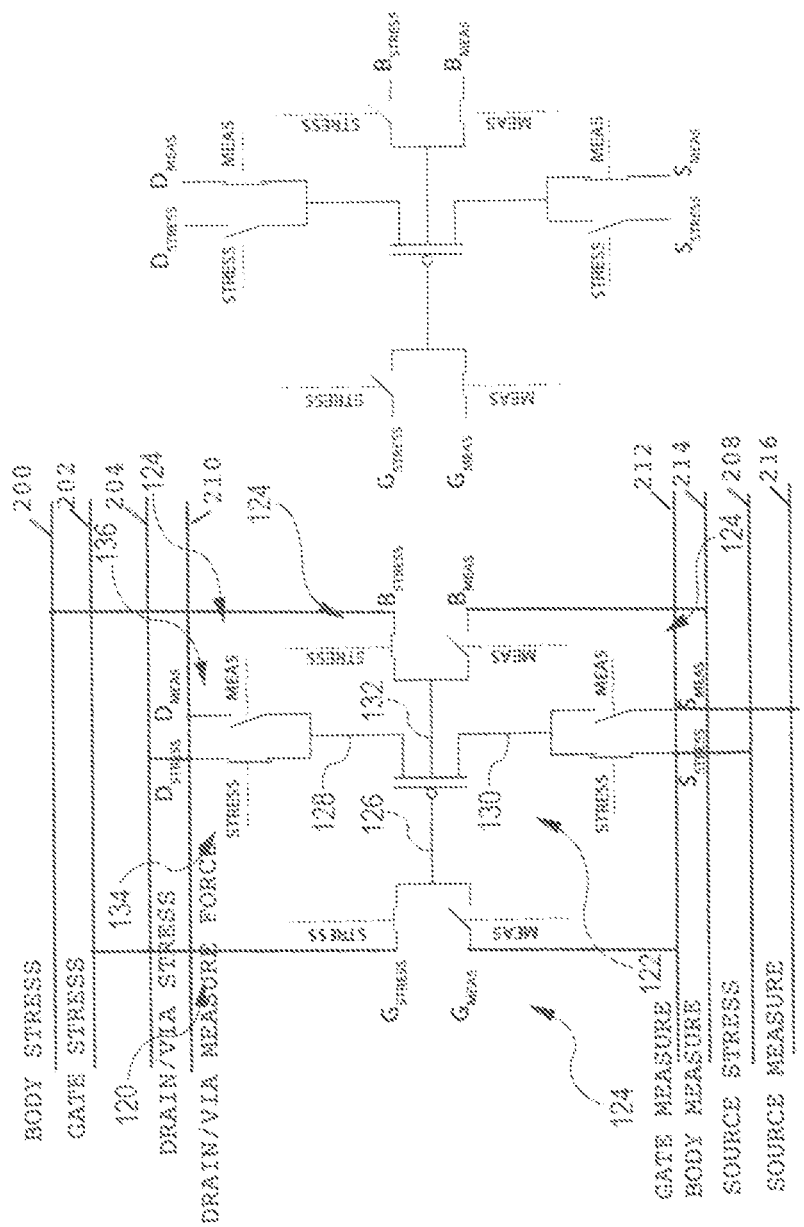

PROGRAMMABLE TEST CHIP, SYSTEM AND METHOD FOR CHARACTERIZATION OF INTEGRATED CIRCUIT FABRICATION PROCESSES

CROSS-REFERENCE TO RELATED APPLICATIONS

This application claims benefit of priority under 35 U.S.C. 119(e) to U.S. Provisional Application No. 61/465,463 entitled "Method and System for Intrinsic Reliability Characterization of Integrated Circuit Fabrication Processes" and filed on Mar. 21, 2011, the entire contents of which are incorporated by reference.

BACKGROUND OF THE INVENTION

1. Field of the Invention

This invention relates to reliability characterization of integrated circuit (IC) fabrication processes, and more particularly to a programmable test chip, system and method for characterization of process variation and reliability of IC fabrication processes at the wafer, die or package levels.

2. Description of the Related Art

Increasing the performance of integrated circuits (ICs) requires a complete and accurate characterization of the variation and reliability of available IC fabrication processes. Established processes must be characterized to provide an IC designer with the information required to selected the appropriate process, specify tolerances of component devices, specify circuit performance, reliability and life time. Historically, IC fabrication processes have evolved to create new processes about every 18 months.

Process selection for a new IC product typically starts with an extensive study of initial process variation and device aging unique to that process. Device degradation will accumulate over time and with use and results in a continuous change in the electrical properties of transistors. Modern nanotechnology CMOS circuits have numerous reliability concerns that have to be accounted for during design and verification cycles. The circuits age during the operational life due to effects such as negative and positive bias temperature instabilities (NBTI, PBTI), time-dependent dielectric breakdown (TDDB), stress-induced leakage current (SILC), hot carrier injection (HCI) damage, electromigration (EM), and stress migration (SM). The varying temperature extremes experienced by circuitry during operation also affects overall reliability.

The process of characterizing any given IC fabrication process requires the fabrication of dedicated test devices in that target process. These devices are measurement circuits that are designed to measure device degradation. Electrical and thermal stress is applied to accelerate one or more failure modes. A program for accelerated life testing is then put into action so that the failure mechanisms can be recorded to generate a rate model for a bathtub curve. Failure mechanisms are accelerated by a number of means including the creation of a specific electrical stress bias and/or exposing the device to an extreme thermal environment. But transistors are 3 or 4 port devices and there is no single bias condition that activates all the different aging mechanisms simultaneously. Some failure mechanism are more relevant than others for a given application, so test devices are developed with specific dimensions and stress configurations to emphasis certain types of degradation. Thus, the characterization process is very much tailored to a specific IC fabrication process and product design objective.

In order to have accurate data to characterize process variation and lifetime, a statistically relevant number of devices, perhaps with multiple geometries, for multiple types of devices (e.g. pMOS and nMOS transistors and vias for a CMOS process) must be tested for multiple failure modes. Existing wafer, die and package-level systems subject test devices to a test either one device at a time or in parallel using expensive parallel probes and complex test systems. Package-level systems require multiple packaged test chips, each including a few test devices, in order to tests tens of the devices.

SUMMARY OF THE INVENTION

The following is a summary of the invention in order to provide a basic understanding of some aspects of the invention. This summary is not intended to identify key or critical elements of the invention or to delineate the scope of the invention. Its sole purpose is to present some concepts of the invention in a simplified form as a prelude to the more detailed description and the defining claims that are presented later.

The present invention provides a test chip, system and method for testing large numbers of test devices on a single test chip to characterize an IC fabrication process, decreasing the time and complexity required to characterize the variation and reliability of the IC fabrication process. This is accomplished with a remotely configurable test chip that can be programmed with varying bias conditions for testing of process variation or numerous failure modes on large sample sizes. An on-chip addressing technique allows large numbers of test devices to be tested simultaneously and the measurement signals read out serially for different test devices. The test chip may be configured for wafer, die or package-level testing.

In an embodiment, a test chip comprises a die fabricated with an IC fabrication process. The die is fabricated with a plurality of devices under test (DUTs), each DUT including a test device having one or more terminals and one or more switch blocks. Each switch block includes a measurement switch coupled between one of the terminals and a measurement contact that provides access for off-chip analog current or voltage meters to the device terminal. Each switch block may include a second measurement switch coupled between the same terminal and a different measurement contact to measure a bias condition at the terminal for purposes of calibration. Each switch block may also include one or more stress switches coupled between the same terminal and different stress contacts to receive bias signals from off-chip analog or current sources. Local resistive heating elements may be fabricated on the die to provide localized heating to accelerate degradation. An addressing circuit on the die couples addressing contacts to the DUT switch blocks to selectively apply stress to groups of test devices and pass one or more measurement signals for a selected test device to the one or more of the measurement contacts for a sequence of different selected test devices. The addressing circuit may comprise single or dual serial registers or line decoders, for example.

In an embodiment, a method of characterizing IC fabrication process comprises providing a test chip, connecting off-chip analog current or voltage sources and analog current or voltage meters to one or more of the measurement contacts on the chip and applying a sequence of digital measurement selection commands for the plurality of DUTs to one or more addressing contacts on the chip to control the DUT switch block measurement switches to selectively bias and pass one or more measurement signals for a selected test device through the one or more of the measurement contacts to the current or voltage meters for a sequence of different selected test devices. The method may also include controlling DUT switch block stress switches to selectively apply bias from off-chip analog sources to stress one or more groups of test devices.

In an embodiment, a system for characterization of an IC fabrication process comprises a test chip, a host controller configured to display a user interface for selection of test modes and specification of test conditions to define a test procedure and to display test data from the test procedure, and a benchtop tester for executing the test procedure on the test chip. The benchtop tester includes programmable voltage and current stress sources, programmable voltage and current measurement sources, voltage and current meters, and an addressing circuit arranged in a universal interface, an adaptor having an input interface that mates with the universal interface and an output interface that mates with the common sets of contacts on the test chip, and one or more controllers responsive to the selected test modes and specified test conditions to program the sources and to control the addressing circuit to applying a sequence of digital measurement selection commands to the test chip.

These and other features and advantages of the invention will be apparent to those skilled in the art from the following detailed description of preferred embodiments, taken together with the accompanying drawings, in which:

BRIEF DESCRIPTION OF THE DRAWINGS

FIGS. 2a and 2b are taken together a diagram of a graphic user interface for selection of tests and specification of test conditions:

FIGS. 9a and 9b are diagrams of a DUT including a pMOS transistor with four switch blocks coupled to its G, D, S and body terminals under stress and measurement bias conditions, respectively;

DETAILED DESCRIPTION OF THE INVENTION

The present invention provides a test chip, system and method for testing large numbers of test devices on a single test chip to characterize an IC fabrication process, decreasing the time and complexity required to characterize the variation and reliability of the IC fabrication process. This is accomplished with a remotely configurable test chip that can be programmed with varying bias conditions for testing of process variation or numerous failure modes on large sample sizes. An on-chip addressing technique allows large numbers of test devices to be tested simultaneously and the measurement signals read out serially for different test devices. The test chip may be configured for wafer, die or package-level testing. Without loss of generality, embodiments of the test chip will be described for package-level testing. The term "contact" may be used to refer to contact pads on the die or the external pins of the package.

Figure 1:
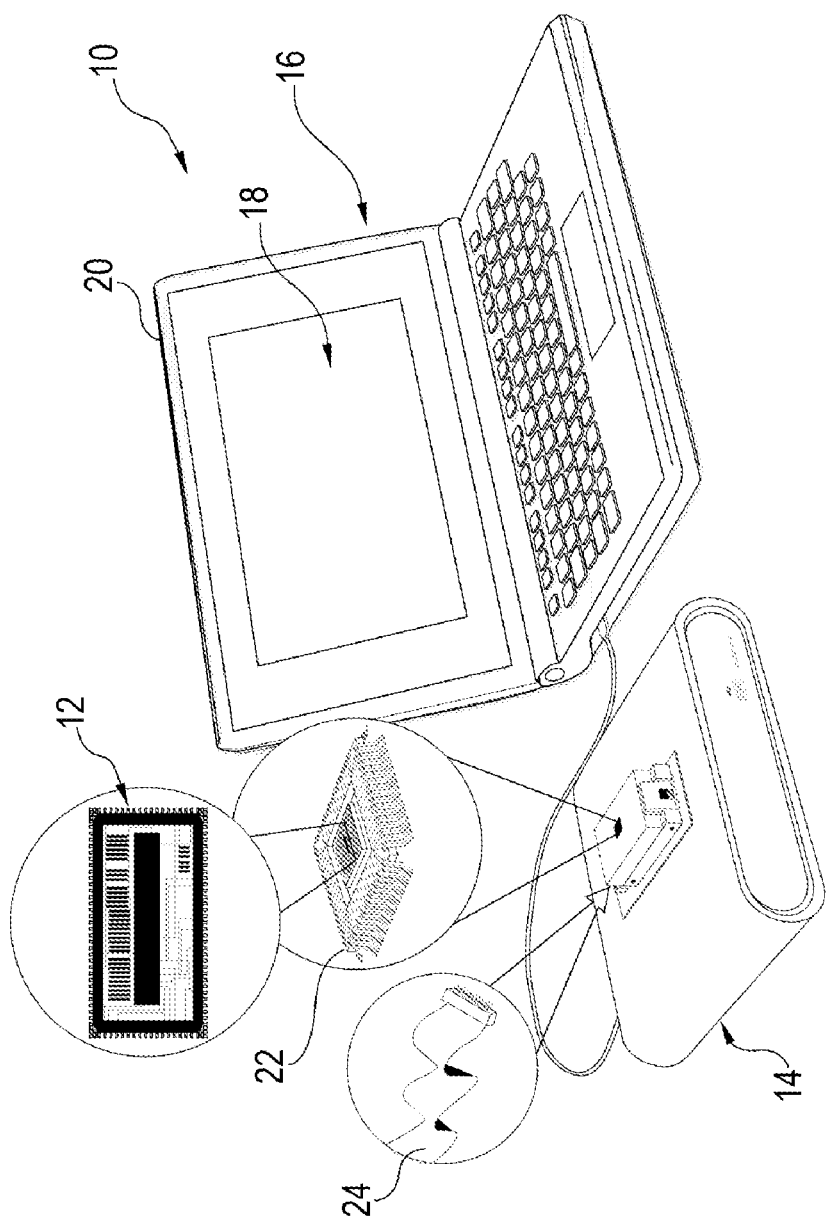
FIG. 1 is a diagram of an embodiment of a system including a host computer, a benchtop tester and a test chip.

Referring now to FIG. 1, a test system 10 includes a test chip 12, a benchtop tester 14 and a host controller 16. The system is constructed hierarchically starting at a graphic user interface (GUI) 18 running on a host computer 20 to provide host controller 16 and going down to the test device level. Down to the benchtop tester, the elements of this system are universal and can be applied to any purpose without additional customization. The test chip includes standardized test devices, switch blocks, logic blocks (depending upon the addressing scheme) and possibly local heaters that are portable. After the test chip is generated once on a given foundry process, it is standard for that process. Different applications may require looking at different failure and aging modes, but all this can be accomplished using the same test chip. Thus, the test chip can be repeatedly copied and used for any purpose or qualification test objective thereafter, as long as it is targeted to that one process.

Test chip 12 comprises a die fabricated with an IC fabrication process. The die is fabricated with a plurality of devices under test (DUTs), each DUT including a test device having one or more terminals and one or more switch blocks. Each switch block includes a measurement switch coupled between one of the terminals and a measurement contact that provides access for off-chip analog current or voltage meters to the device terminal. Each switch block may include a second measurement switch coupled between the same terminal and a different measurement contact to measure a bias condition at the terminal for purposes of calibration. Each switch block may also include one or more stress switches coupled between the same terminal and different stress contacts to receive bias signals from off-chip analog or current sources. Stress is applied to and measurement made from all the DUTs through common sets of stress and measurement contacts. Local resistive heating elements may be fabricated on the die to provide localized heating to accelerate degradation. An addressing circuit on the die couples a common set of addressing contacts to the DUT switch blocks to selectively apply stress to groups of test devices (if applicable) and pass one or more measurement signals for a selected test device to the one or more of the measurement contacts for a sequence of different selected test devices. These measurement signals may provide process variation or degradation for a large sample of test devices. The addressing circuit may comprise single or dual serial registers or line decoders, for example. All of the circuits on the die except the test devices, including the addressing circuitry, switch blocks and logic blocks are fabricated from high voltage rated transistors in the IC fabrication process so that these circuits do not degrade and affect the test results. In this embodiment, the die is packaged to form a packaged test chip having a plurality of external pins that are connected to respective contacts on the die.

Benchtop tester 14 is a specially designed tester instrument with hardware that is used to perform the tests on the DUTs on the test chip. Benchtop tester 14 contains a programmable controller (e.g. one or more microcontrollers or FPGAs) and two plug-in daughter cards that contain components that are needed for the generation of the bias voltages and currents (programmable voltage and current sources) and for measuring currents and voltages (current and volt meters) indicative of process variation or degradation. Tester includes an adapter having an input interface that mates with a universal benchtop interface and an output interface that mates with the test chip. For a packed test chip, the adapter may be an interface card 22 having externals pins that plug into a socket in the tester or may be a ribbon cable 24 having a connector that connects to a mating connector on the tester. The ribbon cable may be useful if, for example, the test chip is placed in an environmental chamber (e.g. radiation exposure) for testing. For wafer or die-level testing, the adapter will interface to a probe station to contact the contact pads on the die. The probes will, however, only need to be contacted to the pads once to perform all of the tests on all of the DUTs. The tester's programmable controller controls test chip 12 and interfaces with host controller 16. The controller is common to all processes and is compatible with all specific test chips. All control functions and measurement processes are moved out of the test chip and into the benchtop tester.

Host controller 16 comprises host computer 20 configured with a software application to control a GUI 18, to communicate with benchtop tester 14 and to process data. Host controller 16 controls the benchtop tester. In other embodiments, the host controller and benchtop tester may be combined in an integrated tester. Host controller 16 provides control and configurability of the test chip, an interface between a human user and the test data and the capability to process the measurement data into a more useful format such as process variation or lifetime estimates. The host controller communicates to the programmable controller on the benchtop tester what tests to run, the test conditions and DUTs to be tested. All the monitoring objectives are set up by the host controller through, for instance, GUI 18.

The host controller 16 is suitably attached to the benchtop tester by a serial bus interface. Data communication is asynchronous, e.g. RS-485 or USB 2.0. But it could also be RF, GPIB 488, Ethernet, Etc. Communication between the benchtop tester and the test chip is more direct. In an embodiment, an asynchronously clocked serial data line(s) is used to control hundreds or thousands of DUTs simultaneously on the chip. In another embodiment, an asynchronously clocked line decoder(s) may be used to control the DUTs. The communication between the benchtop tester and the test chip is analog for the stress current and voltage waveforms and the measurement signals. The one or more measurement signals are generated in sequence on the test chip for different DUTs and read out through one or more measurement pins. In this manner, a large number of DUTs may be addressed and tested on a single packaged test chip through a limited number of addressing, stress and measurement pins. The number of DUTs test may far exceed the number of pins on the packaged test chip.

Figure 2A:
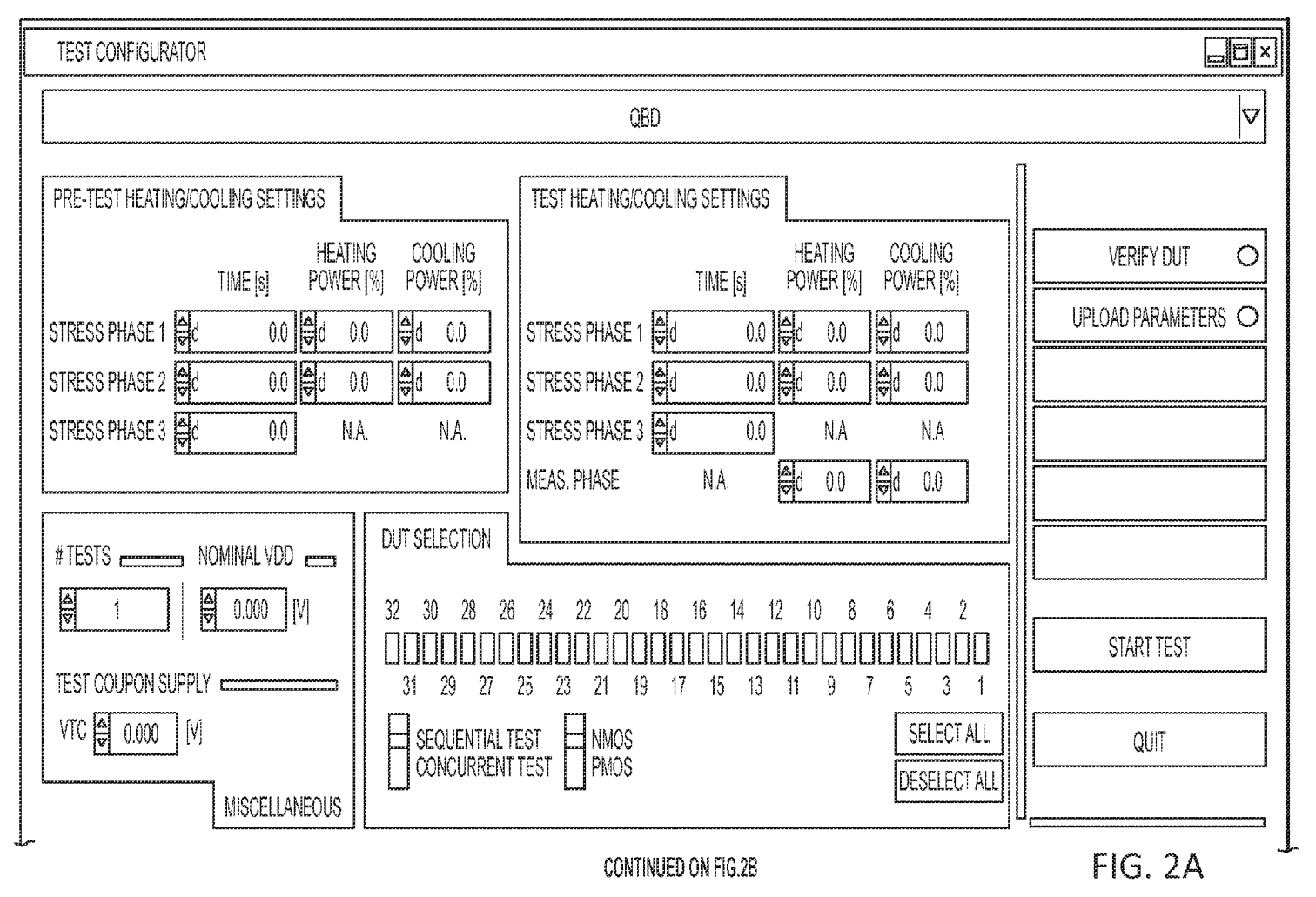
Figure 2B:
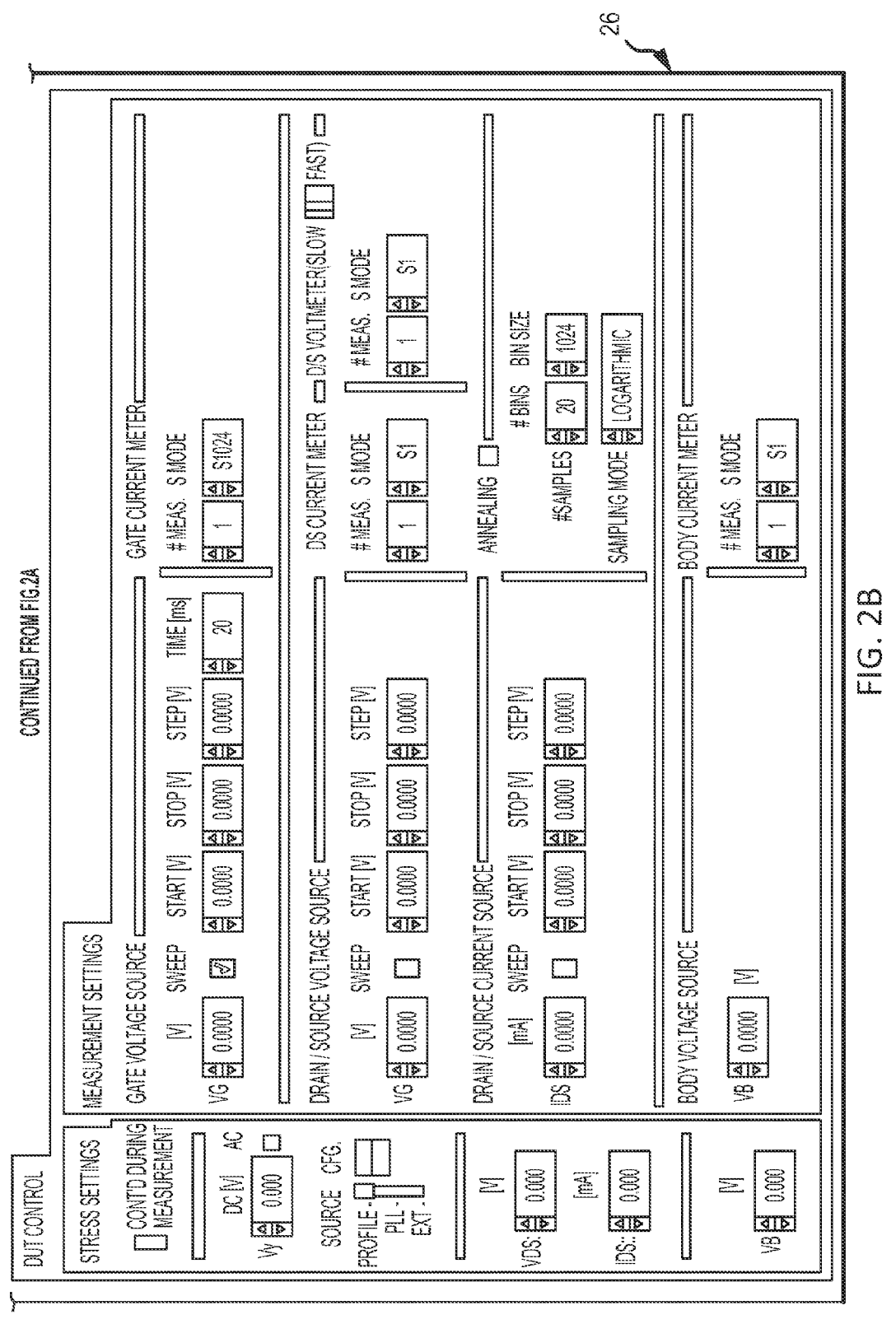

An exemplary test control panel 26 for GUI 18 is shown in FIGS. 2a and 2b. This particular panel is created for the charge to break down (QBD) tests for NMOS and PMOS DUTs. The control panel allows the user to select the test voltages, currents, temperature and other needed parameters for "Stress Settings" and "Measurement Settings" with "DUT Control" and to select the DUT arrays that will be subjected to the test as well as the individual DUTs that will be measured during the test "DUT Selection". The GUI also facilitates specification of Pre-Test and Test "Heating/Cooling Settings". DUTs may be grouped into linear "arrays" to facilitate testing. For example, PMOS transistors, NMOS transistors and vias used to conduct current between different metal layers in an IC may be formed into three separate arrays. Each of these may be further separated into additional arrays for testing different failure modes or for different geometries of the test devices.

Figure 3:
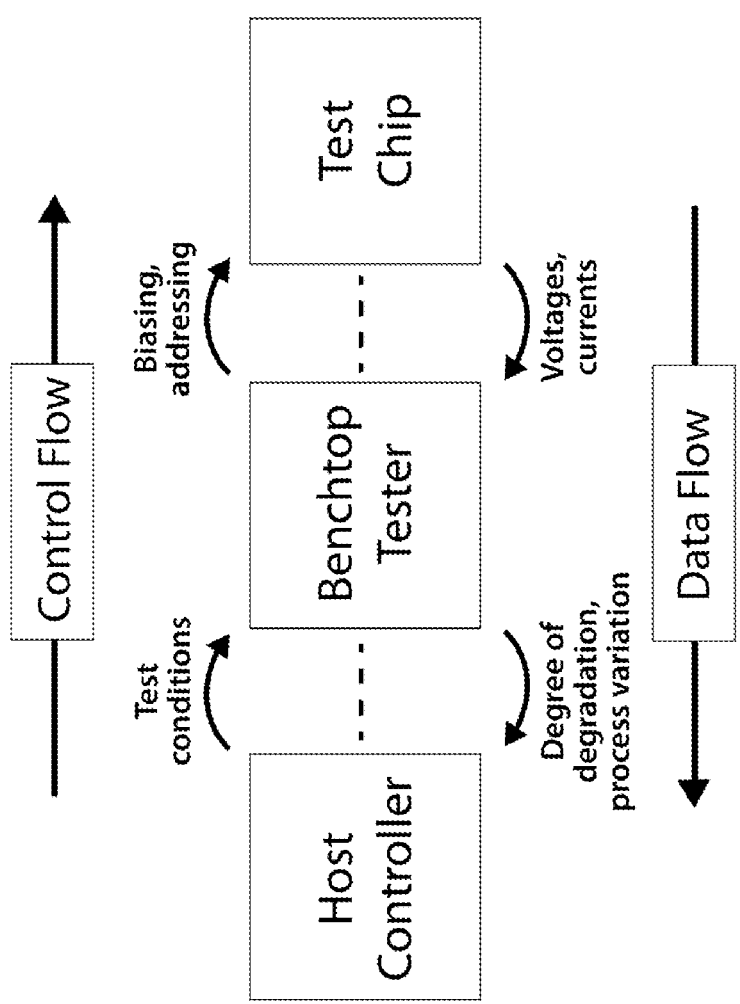
FIG. 3 is a control flow and data flow diagram between system components.

The control flow and data flow between host controller 16, benchtop tester 14 and test chip 12 is illustrated in FIG. 3. The tests to be performed, test conditions, DUTs tested and DUTs measured are passed from the host controller to the benchtop tester. The tester formats this information into a sequence of biasing signals and addressing selection commands that are applied to the stress and measurement pins and addressing pins of the test chip. The test chip applies the same or different stress conditions (if specified) to one or more arrays of DUTs and selectively passes one or more measurement signals (e.g. voltages, currents) from a selected DUT through measurement pins back to the benchtop tester for a sequence of different selected test devices. Typically, the host will specify a test procedure in which the first test is to measure one or more data parameters without stress in order to compute process variation. Thereafter, the test procedure will specify different tests of degradation mechanisms over time to assess reliability. The benchtop tester may return raw data to the host controller or an external memory such as USB memory stick or SD memory card. Alternately, the tester may perform some amount of processing on the data to provide measures of process variation or device degradation for a particular test.

In an embodiment, information related to the process or test chip may be electronically stored on the test chip and electronically polled by the benchtop tester. This data would be hardwired and permanently stored in binary format and encoded, for example, by customization of one of the metal mask layers. This information can be accessed by the benchtop tester to identify the process being tested and other configuration information that is stored on the test chip such as tests to run, test conditions, DUTs to stress and DUTs to measure. The host controller and benchtop tester may also write information to the memory to specify test information such as tests completed and DUTs tested. In general, once DUTs are stressed, hence degraded to perform a particular test they are not reused.

Figure 4:
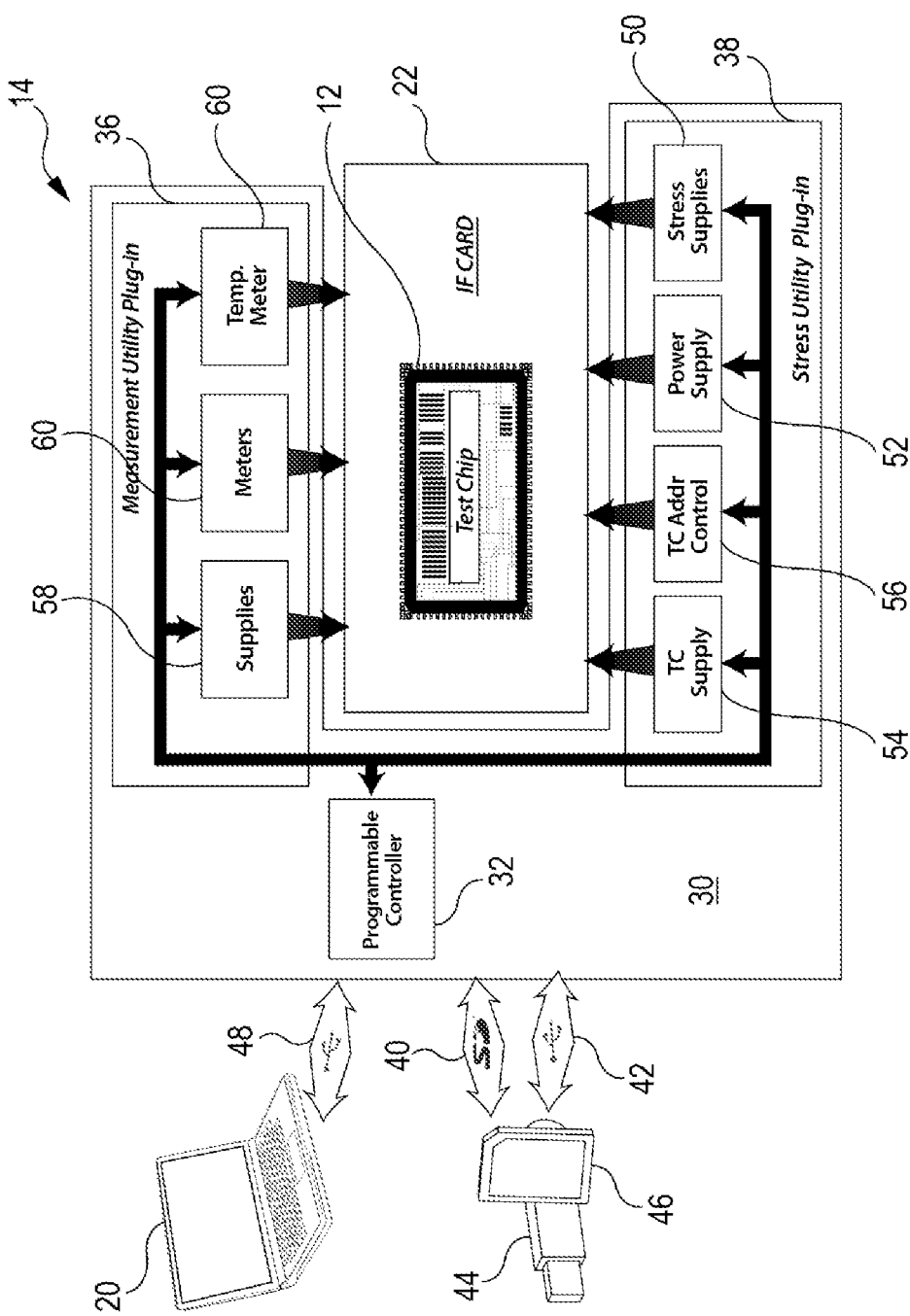
FIG. 4 is a block diagram of an embodiment of the benchtop tester.

As shown in FIG. 4, an embodiment of benchtop tester 14 contains a main card 30 with a programmable controller 32 (e.g. one or more microcontrollers or FPGAs), and three daughter cards including test chip interface card 22, a measurement utility plug-in card 36 and a stress utility plug-in card 38. The main card holds programmable controller 32 and sockets 40 and 42 to external USB memory sticks 44 and SD memory cards 46, respectively, and a USB interface 48 to host computer 20. When these external memories are used the benchtop tester does not need to be connected to the host during the test. The main card also includes an analog-to-digital (ADC) converter to convert measurement signals to digital data. Stress card 38 holds programmable stress supplies (analog voltage and current sources) 50 that are specific for providing stress waveforms to the test chip. Card 38 also includes a power supply 52 for delivering power to local heaters on the test chip to accelerate degradation. The power supply may be capable of providing either DC current or pulse width modulated (PWM) for heating. Card 38 also includes a test chip supply 54 to provide power to the test chip and addressing control 56 to format the addressing selection commands for the test chip. Measurement card 36 holds programmable measurement supplies (voltage and current sources) 58, and analog meters (voltage and current meters) 60 that are needed in the different parameter measurements and temperature meters 62 to measure the localized temperature of the DUTs and DUT arrays. The measurement sources and meters may be hybrid components capable of both sourcing and measuring. For example, a source may force voltage and measure current or force current and measure voltage. For the greatest capability, each measurement pin is preferably capable of both source and measurement. The various supplies, meters and addressing control of the stress and measurement boards are arranged in a universal interface for all test chips and processes.

Interface card 22 has a universal input interface that mates with the benchtop tester's universal interface (e.g. standardized pin out) and an output interface (e.g. socket or contact pads) that mates with the pin out of a particular test chip. The card's output interface connects supply 54 to the supply pins on the test chip, addressing control 56 to a first common set of addressing pins on the test chip, the measurement supplies 58 and meters 60 to a second common set of measurement pins on the test chip and the stress supplies 50 to a third common set of stress pins on the test chip. Other stress supplies 50 may be connected to a fourth common set of stress pins to allow for simultaneous stressing of different DUT arrays under different bias conditions. A different interface card 22 may or may not be required for test chips associated with different processes. The test chip 12 is attached to the interface card 22 by placement inside a re-usable non-permanent chip socket, or directly soldered onto contact pads on the card.

The on-chip addressing technique allows large numbers of test devices to be tested simultaneously and the measurement signals read out serially for different test devices. An addressing circuit on the die couples a common set of addressing contacts to the DUT switch blocks. The addressing circuit may comprise single or dual serial registers or line decoders, for example. The benchtop tester's addressing control applies a sequence of digital measurement selection commands for the plurality of DUTs to one or more addressing contacts to control the DUT switch block stress switches to selectively bias a group of test devices and to control the DUT switch block measurement switches to selectively bias and pass one or more measurement signals for a selected test device through the one or more of the measurement contacts to the benchtop tester's current or voltage meters for a sequence of different selected test devices. In this manner, a large number of DUTs may be addressed and tested on a single packaged test chip through a limited number of addressing, stress and measurement pins. The number of DUTs test may far exceed the number of pins on the packaged test chip.

Figure 5A:
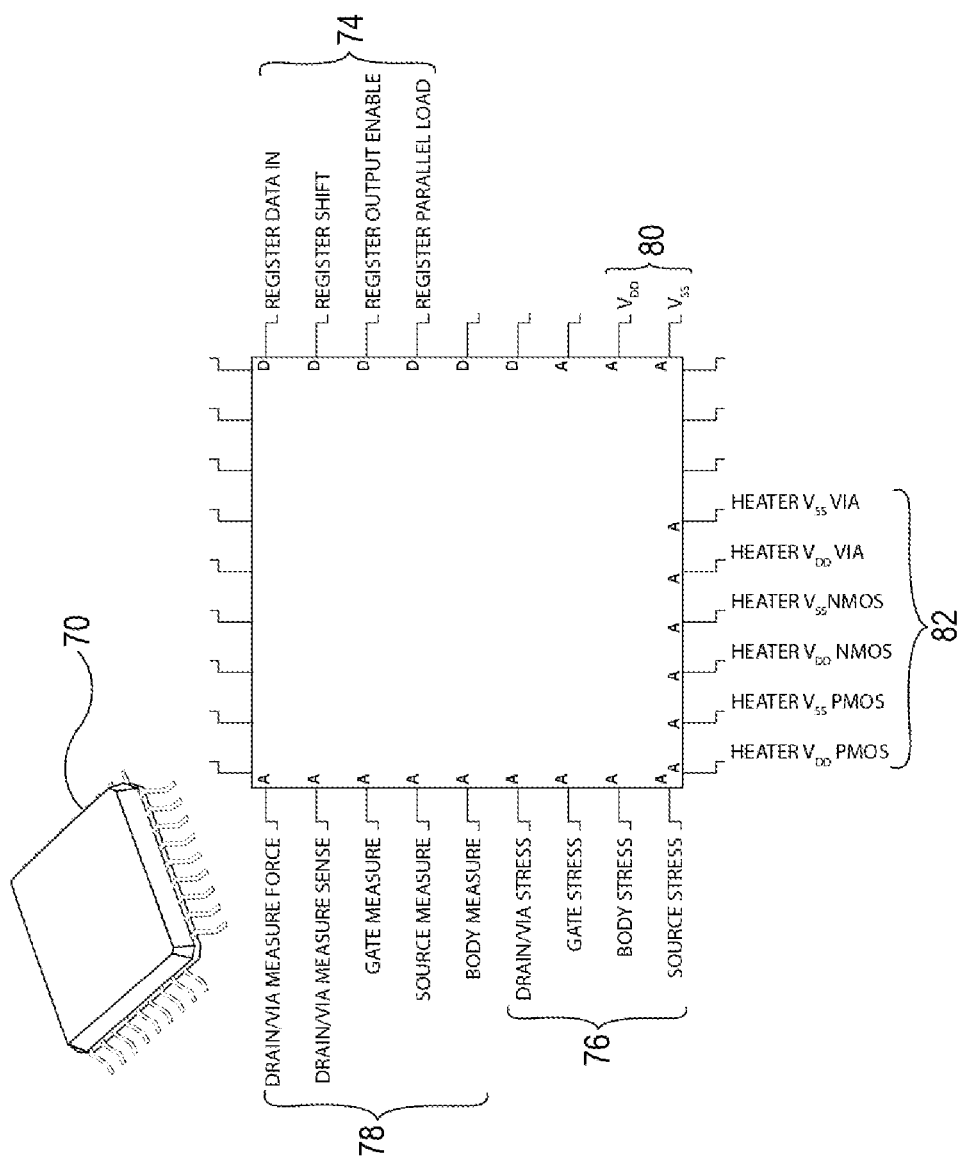
FIGS. 5a and 5b are diagrams of the external pin out and registers for an embodiment using a single serial register to address DUTs.
Figure 5B:
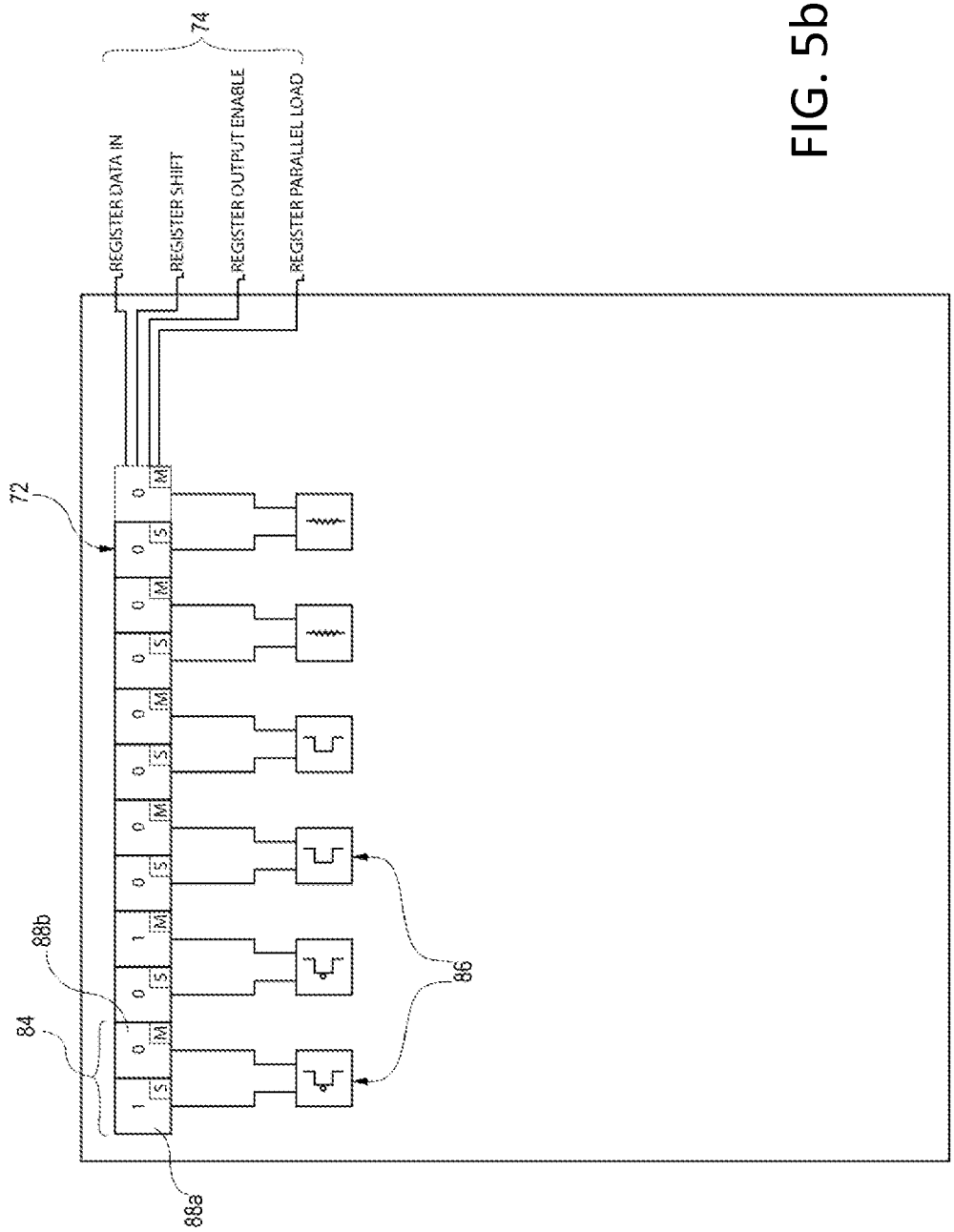

An embodiment of a packaged test chip 70 and implementation of the addressing circuit with a single serial register 72 is illustrated in FIGS. 5a-5b. The package pins that are connected to digital control signals on the benchtop tester are labeled with "D". A common set 74 of digital pins (REGISTER DATA IN, REGISTER SHIFT, REGISTER OUTPUT ENABLE, REGISTER PARALLEL LOAD) together pass the serial digital control bits from the benchtop tester onto the test chip. The actual selection commands (data) is input on the single REGISTER DATA IN pin for all of the DUTs. The other digital pins are used to get the selection commands (data) loaded into the serial register. The package pins that are connected to analog voltage or current sources or meters on the benchtop tester are labeled with "A". A common set 76 of analog pins pass the analog stress bias currents or voltages generated on the benchtop tester daughter cards onto the packaged test chip. A common set 78 of analog pins pass the analog measurement bias currents or voltages generated on the benchtop tester daughter cards onto the packaged test chip. Some of these analog pins also connect the measurement devices, i.e. volt or current meters, placed on the benchtop tester measurement utility plug-in daughter card, onto the chip. VDD and VSS pins 80 are used to connect power supply and ground to the test chip. Heater VDD and VSS pins 82 are used to power up the local degradation accelerating healers that are surrounding the DUTs. There are separate VDD and VSS pins for every DUT array.

Serial register 72 includes a number of cells 84 equal to the number of DUTs 86 on the die. Each cell 84 includes a stress "S" sub-cell 88a and a measurement "M" sub-cell 88b. Each cell 84 is connected to a different DUT 86, and more particularly to its one or more switch blocks. The binary value in S sub-cell 88a is coupled to the control input of the stress switch in each of the one or more switch blocks. The binary value in M sub-cell 88b is coupled to the control input of the measurement switch in each of the one or more switch blocks. In an embodiment, the serial register includes a shift register and,a storage register. The values in these cells, and sub-cells can be changed by shifting new data in serially into the shift register from the REGISTER DATA IN pin. The data is clocked into the shift register with the REGISTER SHIFT signal, loaded in parallel into the storage register with the REGISTER PARALLEL IN signal and enabled for application to the DUTs with the REGISTER OUTPUT ENABLE. The "new data" corresponds to the next entry in a sequence of digital stress and measurement selection commands for the plurality of DUTs. The sequence of data that is shifted into the registers is generated in the benchtop tester instrument that is controlled by the GUI.

A single serial register implementation of the addressing circuit provides the greatest flexibility to apply the stress from a common set of sources to any combination of the DUTs 86 simultaneously. The measurement is normally done one DUT at a time, but it is possible to select multiple DUTs for measurement simultaneously in which case the DUTs would be connected in parallel at the measurement contact. This would be useful, for example, when trying to measure small leakage currents the magnitude of which is so small that a leakage current from just a single transistor cannot be measured accurately with the benchtop tester. The disadvantage of this approach is that as the number of DUTs runs into the thousands the length of the single serial register, hence the time to shift new data into the shift register grows.

Figure 6:
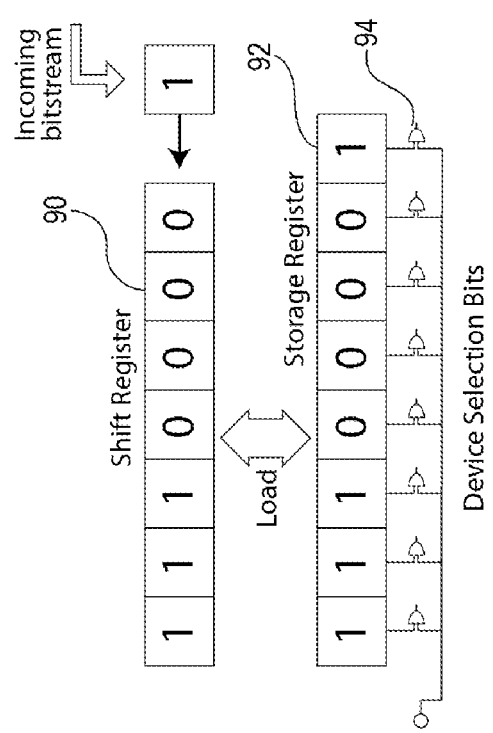
FIG. 6 is a diagram of a serial register.

FIG. 6 illustrates an embodiment for implementing the serial register. An incoming bit stream from the benchtop tester at REGISTER DATA IN can be shifted into a shift register 90 under the control of a clocking signal at REGISTER SHIFT. Once the data is shifted into the shift register 90, the data is loaded in parallel into a storage register 92 under the control of a signal at REGISTER PARALLEL LOAD. Once loaded, the storage registered is enabled as a selection signal to the DUTs by using a standard logic AND gate 94 and setting the REGISTER OUTPUT ENABLE high. The data in storage register 92 that is used to control DUTs does not change as new data is shifted in to shift register 90. This functionality allows performing measurements on some. DUTs, while other DUTs are under stress conditions.

An alternate embodiment, uses a single register. The OUTPUT ENABLE is switched low while data is shifted into the register and then switched high. This provides a simpler register configuration without the need for PARALLEL LOAD. The tradeoff is that testing is suspended during the period of time data is being shifted into the register.

Figure 7A:
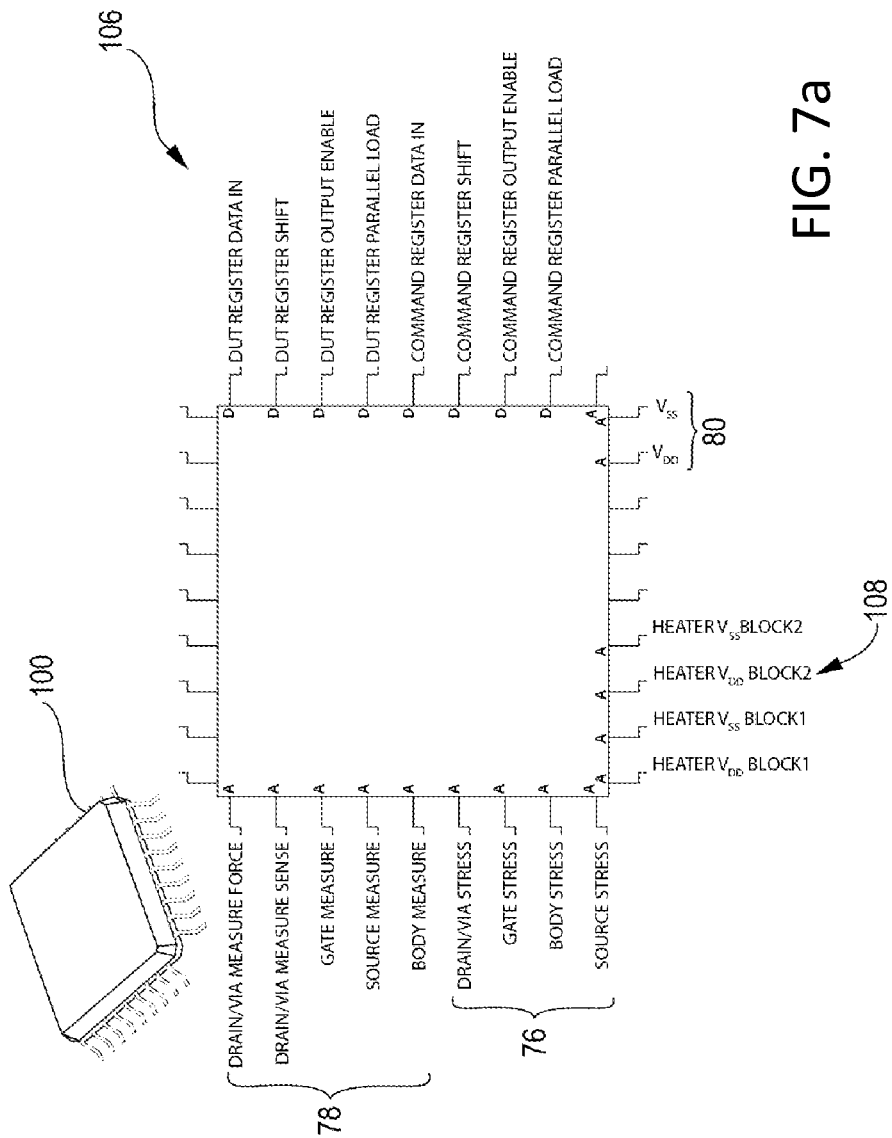
FIGS. 7a and 7b are diagrams of the external pin out and registers for an embodiment using a dual serial register to address DUTs.
Figure 7B:
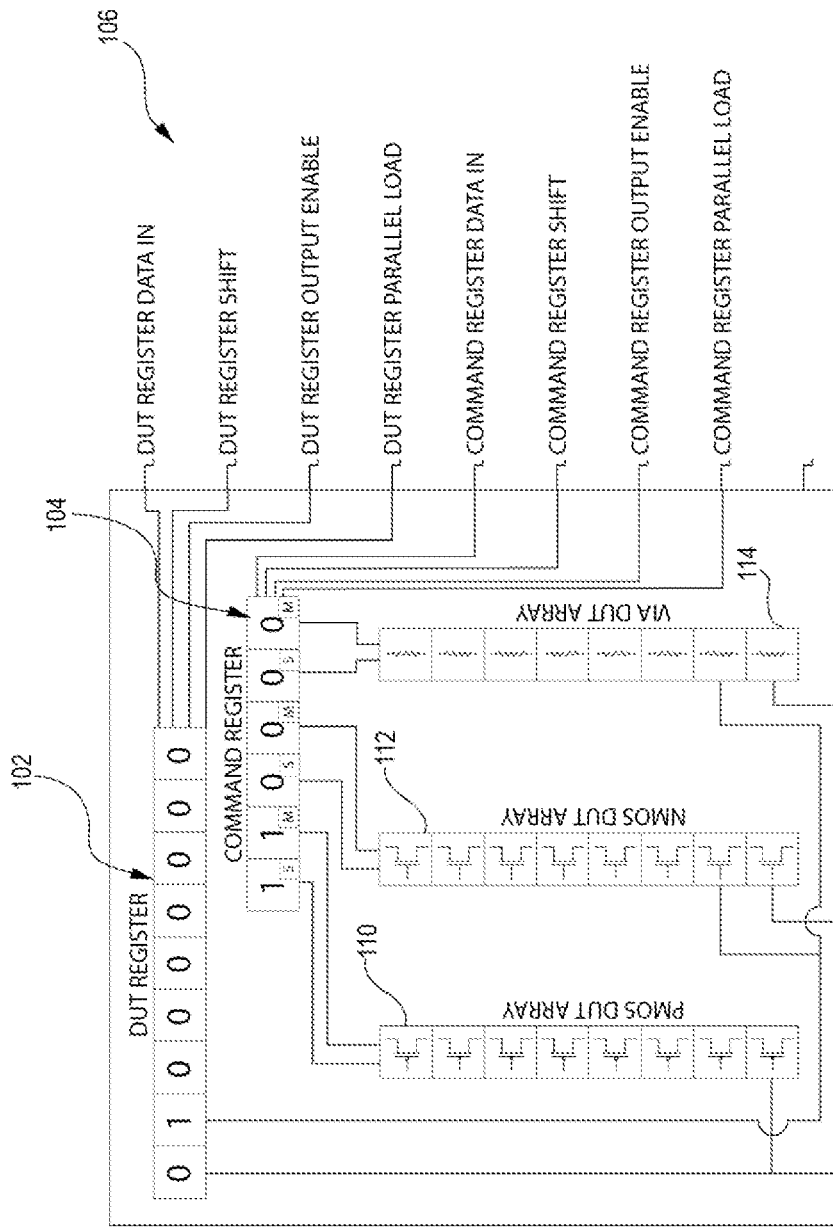
Figure 8:
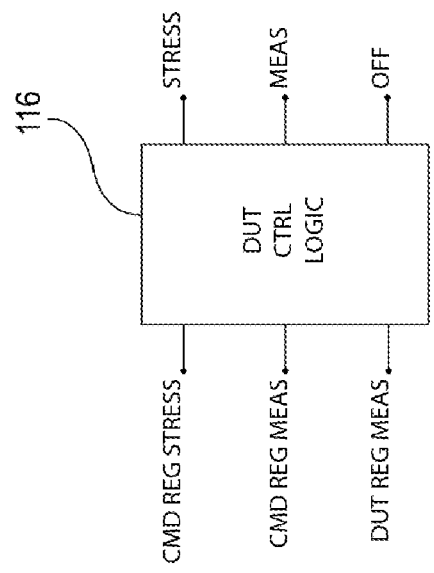
FIG. 8 is a diagram of an embodiment of a logic block within each DUT for decoding selection commands for the dual serial register.

An embodiment of a packaged test chip 100 and implementation of the addressing circuit with a DUT serial register 102 and a command register 104 is illustrated in FIGS. 7a-7b and 8. This dual-register approach is faster than the single register approach, particularly as the number of DUTs gets large, but is limited to applying stress to arrays of DUTs instead of individual DUTs and requires a logic block in each DUT. The analog stress pins 76, measurement pins 78 and power pins 80 are the same as the single register implementation. A common set 106 of digital pins (DUT REGISTER DATA IN, DUT REGISTER SHIFT, DUT REGISTER OUTPUT ENABLE, DUT REGISTER PARALLEL LOAD and COMMAND REGISTER DATA IN, COMMAND REGISTER SHIFT, COMMAND REGISTER OUTPUT ENABLE, COMMAND REGISTER PRALLEL LOAD) together pass the serial digital control bits from the benchtop tester onto the test chip for DUT serial register 102 and command register 104. Heater VDD and VSS pins 108 are used to power up the local degradation accelerating heaters that are surrounding the DUTs. There are separate VDD and VSS pins for every DUT array.

In this example, packaged test chip 100 contains three DUT arrays; a PMOS DUT array 110 of PMOS transistors, a NMOS DUT array 112 of NMOS transistors and a VIA DUT array 114 of vias. Each individual DUT comprises a test device (e.g. PMOS transistor, NMOS transistor or via), one or more switch blocks each including a stress switch, a measurement switch and an off switch and a DUT control logic block 116 as shown in FIG. 8. DUT control logic block 116 decodes the DUT register measurement control bit and the command register stress and measurement control bits to control the stress, measurement and off switches. If the command register stress and either of the measurement control bits are zero, the off switch is closed to ground the terminal of the test device so that it does not float.

DUT register 102 is a serial register that is use to select individual DUTs for measurement. In-this case the register has eight individual cells that store either one or zero. The values in these cells can be changed by shifting new data in serially from the DUT REGISTER DATA IN pin. The values stored (zero or one) in these individual cells control the logic of the DUTs. The first cell in the DUT register is connected to the first DUT in every DUT array, the second cell to the second DUT, etc.

Figure 12:
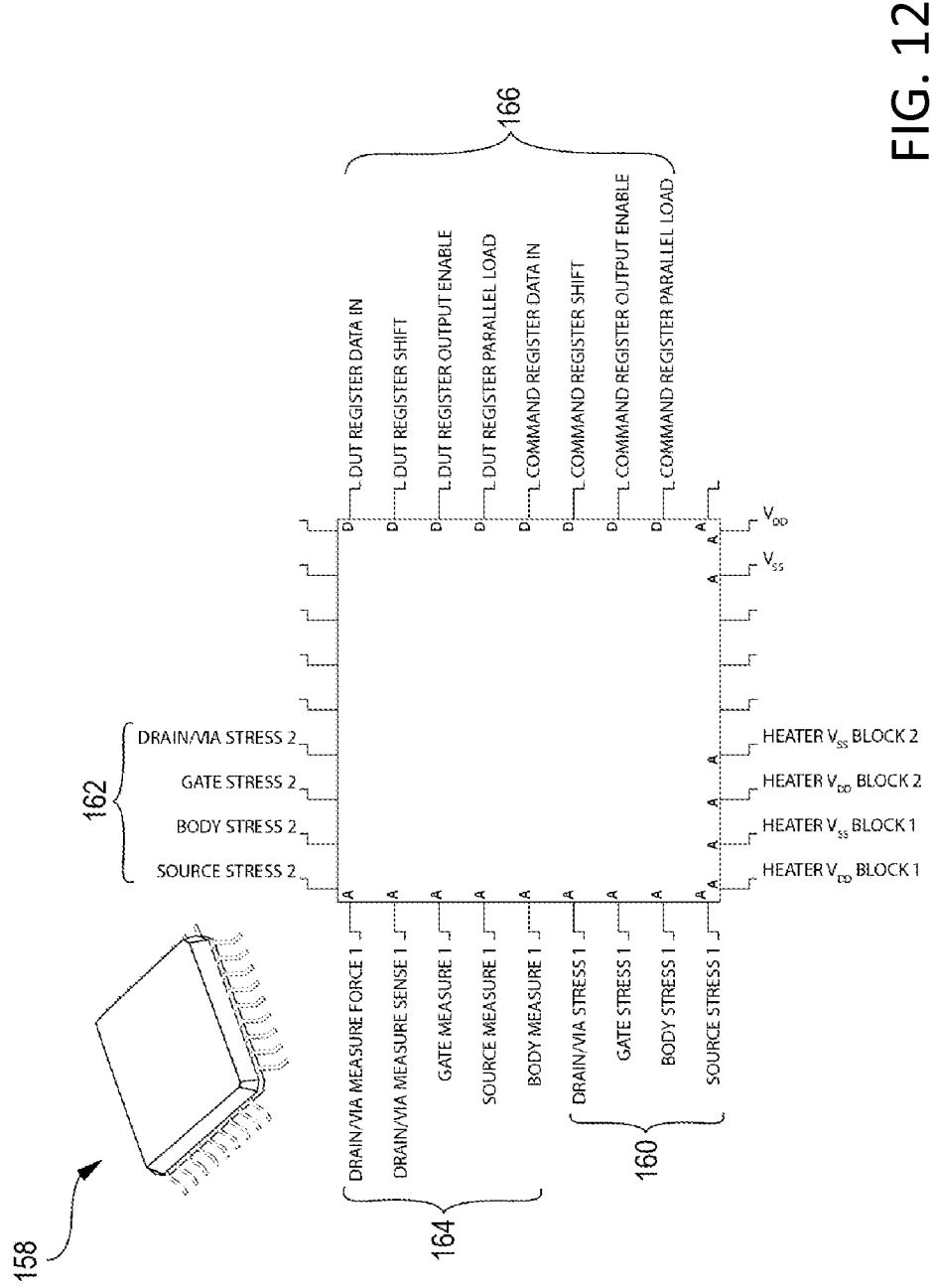
FIGS. 12-14 are diagrams of the pin out, serial register and switch block for an embodiment capable of applying different stress conditions to different groups of DUTs simultaneously.
Figure 13:
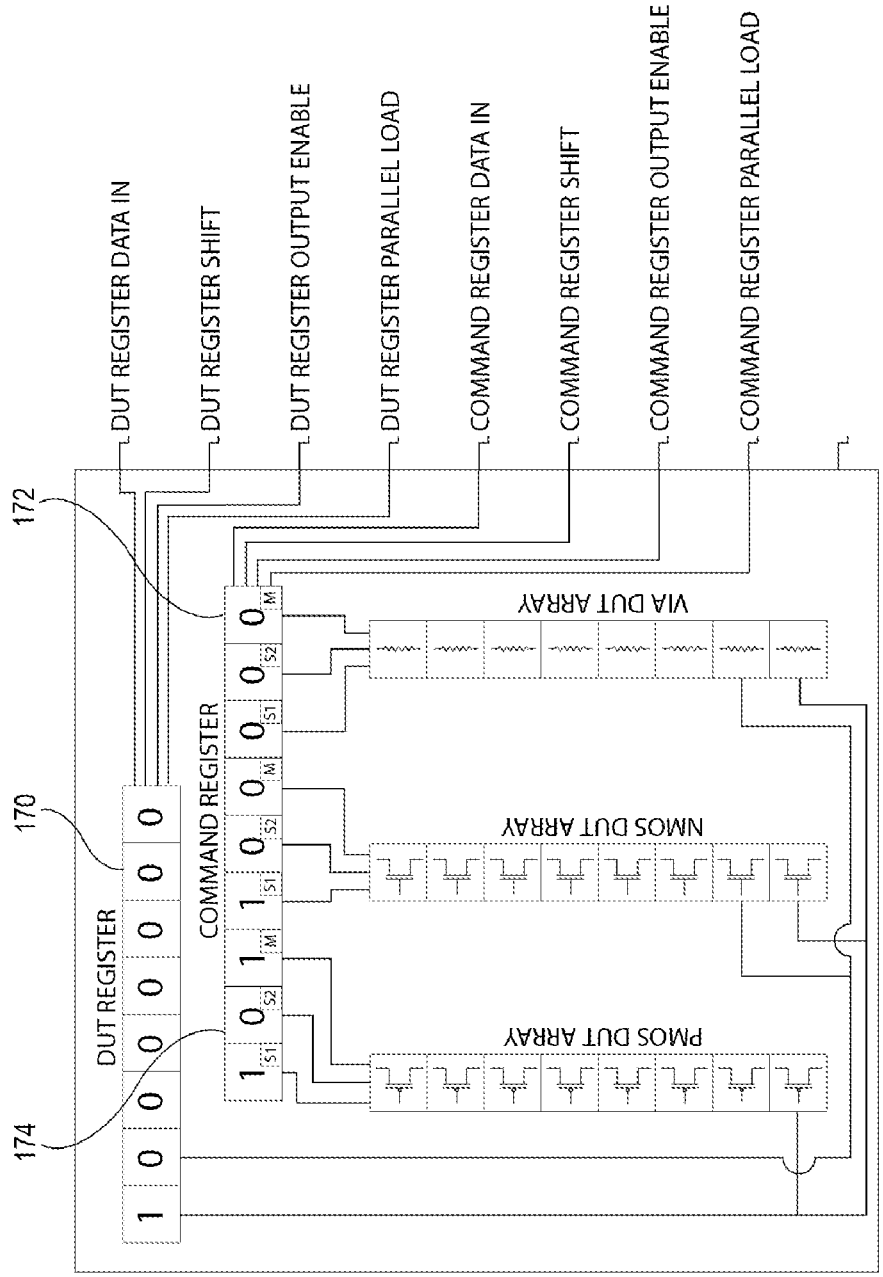
Figure 14:
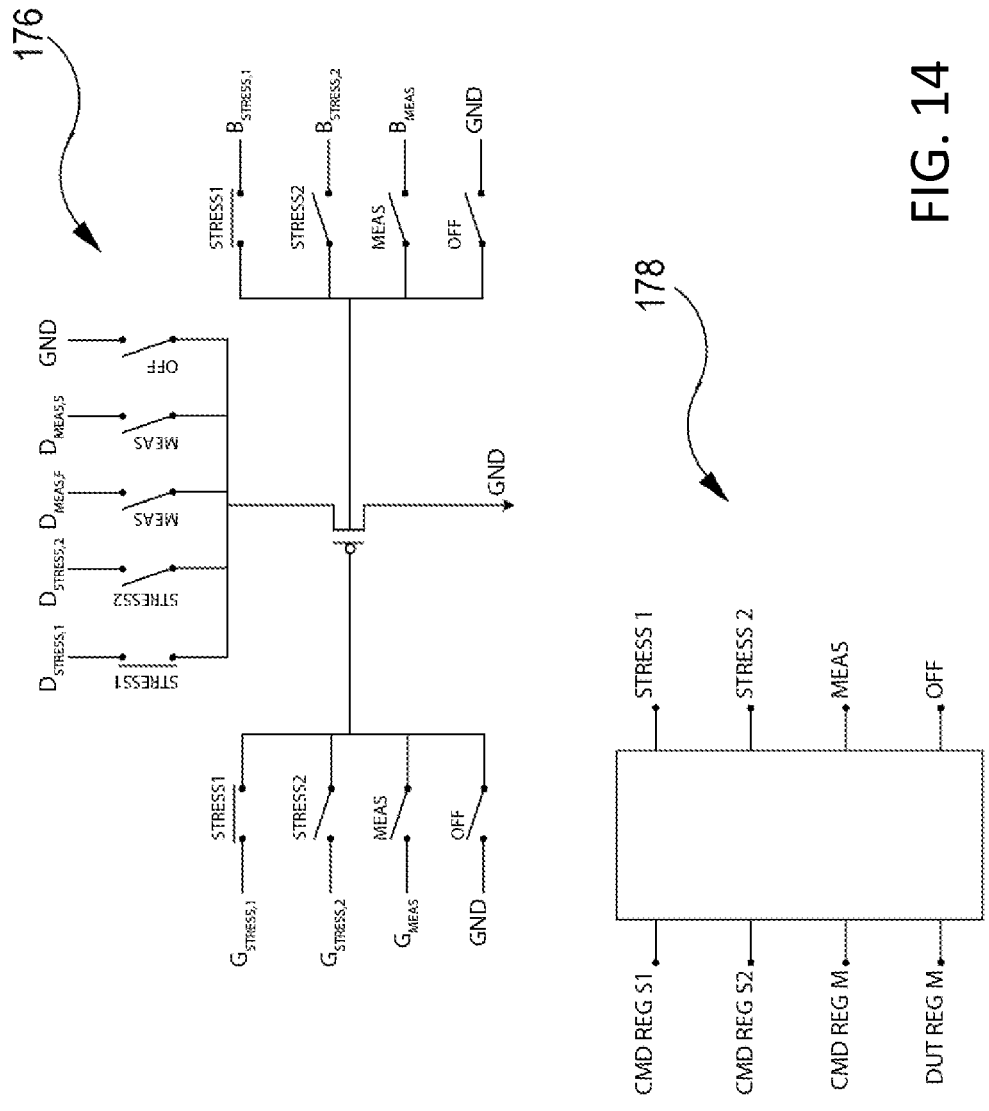

Command register 104 is another similar serial register and the stored values in it are used to select DUT arrays for stress and measurement. In this case the register has three individual cells, each cell including a "S" sub-cell and an "M" sub-cell that control the DUT array selection for stress and measurement. In the configuration shown, all three DUT arrays can be selected for stress simultaneously, the stress being the same for all arrays (a more complex topology in which different test condition can be given to different arrays is illustrated in FIGS. 12-14). The values in these cells can be changed by shifting new data in serially from the COMMAND REGISTER DATA IN pin. The values stored (zero or one) in these individual cells control the logic of the arrays. The first cell in the command register is connected to every DUT in the PMOS DUT array, the second cell in the command register is connected to every DUT in the NMOS DUT array and the third cell in the command register is connected to every DUT in the VIA DUT array. The register structure depicted in FIG. 6 can be used to implement both the DUT register and the command register.

Alternately, each register may be implemented as a single register. DUT control logic block 116 implements the following truth table:

| CMD S | CMD M | DUT M | STRESS | MEAS | Off |
|-------|-------|-------|--------|------|-----|
| 0 | 0 | 0 | 0 | 0 | 1 |
| 0 | 0 | 1 | 0 | 0 | 1 |
| 0 | 1 | 0 | 0 | 0 | 1 |
| 0 | 1 | 1 | 0 | 1 | 0 |
| 1 | 0 | 0 | 1 | 0 | 0 |
| 1 | 0 | 1 | 1 | 0 | 0 |
| 1 | 1 | 0 | 1 | 0 | 0 |
| 1 | 1 | 1 | 0 | 1 | 0 |

The logic block creates a MEAS signal if and only if CMD M and DUT M are high. If MEAS is high, STRESS cannot be high. OFF is high if both MEAS and STRESS are low. The test chip can pick one device from one array for measurement when other devices in the same array are still stressed and devices in other arrays are stressed. The test chip can also pick one device for measurement before and after stress. The OFF state ensures that no stresses are accidentally applied to the devices and that the terminals are not floating during their non-operational period.

FIGS. 9a and 9b shows a simplified topology of a PMOS DUT 120 in its stress and measurement configurations, respectively. DUT 120 includes a PMOS transistor 122 and a switch block 124 connected to each of its Gate, Drain, Source and Body terminals 126, 128, 130 and 132, respectively, Each switch block 124 includes a stress switch 134 and a measurement switch 136 that connect the terminal to stress or measurement pins on the package test chip. Analog buses (200, 202, 204, 208, 210, 212, 214 and 216) are formed on the die to connect each pin to a particular switch and device terminal on all of the DUB. For example, an analog bus connects the top of the gate measurement switch for every DUT to the gate measurement pin, A different analog bus connects the top of the gate stress switch for every DUT to the gate stress pin.

In FIG. 9a, the STRESS switches 134 are closed and thus the DUT is in stress mode, i.e. receiving stress bias voltages or currents from the benchtop tester. In FIG. 9b, the MEAS switches 136 are closed, which means that now the DUT is in measurement mode and it is connected to measurement meter and measurement bias voltages/current sources on the benchtop tester. The control voltages for these switches are the held output voltages by the individual cell in serial register(s). The held output voltages are typically buffered, the buffer may be considered as part of the cell.

Additional CONFIG switches may be connected between terminals of the test device and selectively controlled to reconfigure the device itself. For example, a switch between the Gate and the Drain could be used to form a MOS diode.

Figures 10A, 10B:
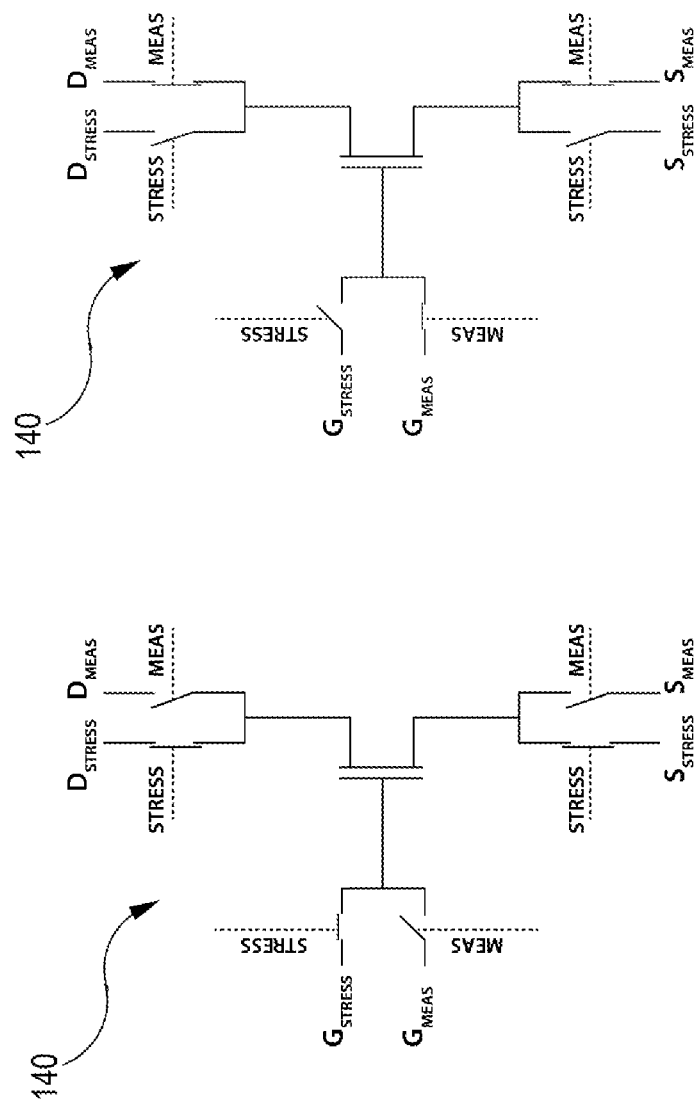
FIGS. 10a and 10b are diagrams of a DUT including a nMOS transistor with three switch blocks coupled to its G, D and S terminals under stress and measurement bias conditions, respectively.

FIGS. 10a and 10b show a simplified topology of an NMOS DUT 140. The topology is similar to the PMOS DUT except that an NMOS transistor does not have a body connection and thus a switch block is not provided to the body terminal.

Figure 11:
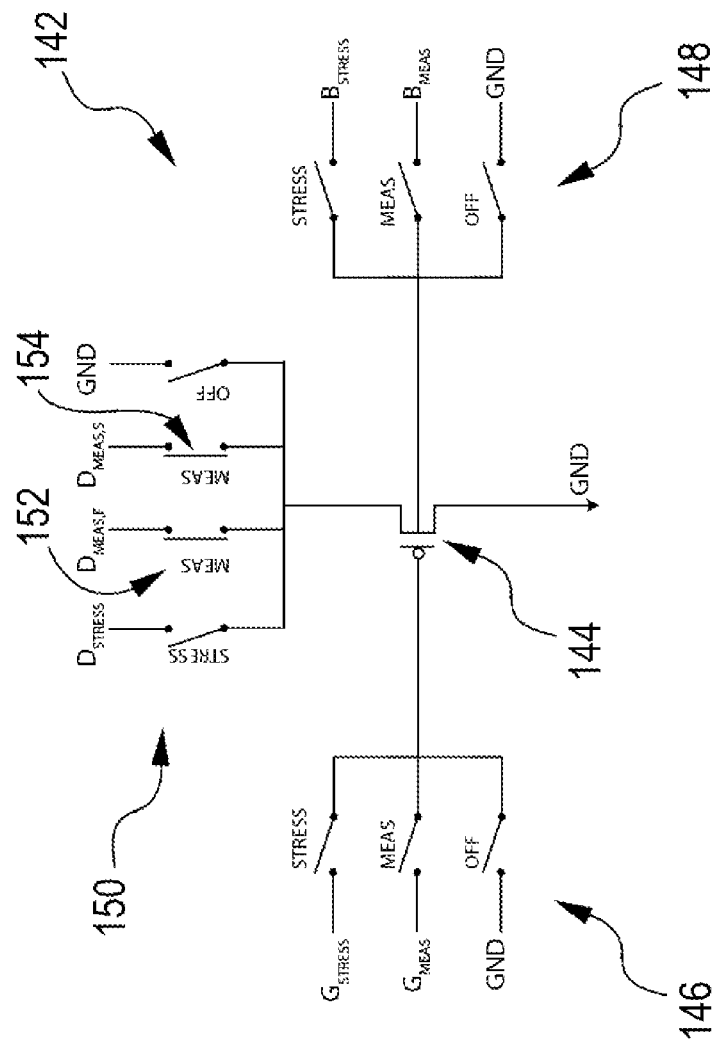
FIG. 11 is a diagram of an alternate embodiment of the switch block for an nMOS transistor including measurement force and measurement sense switches.

FIG. 11 illustrates another embodiment of a DUT 142 including a PMOS transistor 144. Each switch block 146, 148 and 150 includes the STRESS and MEAS switches. Each switch block also includes an OFF switch. The OFF control signal is set to be activated if neither MEAS nor STRESS signals are selected. During this state all the terminals of the DUT are pulled to ground so that no degradation mechanisms are activated. The drain switch block 150 includes a pair of measurement switches; measure-force switch 152 and measure-sense switch 154. The drain current used to bias the device during measurement can cause a voltage drop over the switch on the drain terminal. Thus, the actual DUT terminal voltage will be different than what is generated by the programmable voltage sources of the benchtop tester. It is important to measure this voltage drop so that the correct stress and measurement bias conditions will be recorded. This voltage drop can be measured through parallel measure-sense switch 154 that is connected to a voltmeter on the benchtop tester that has a low measurement current. This volt meter is connected to the test chip package pin $D_{MEAS,S}$ (drain measure, sense) and the measurement bias drain current flows through measure-force switch 152 and the terminal $D_{MEAS,F}$ (drain measure, force). Note that all the needed measurement and stress conditions can be created with grounded source terminal and that is why we have permanently connected this terminal to ground.

The total test time needed for comprehensive IC fabrication process reliability characterization can be considerably shortened by simultaneously applying several different degradation tests on several different DUT arrays on the test chip. The DUTs are still suitably measured one at a time (or in a parallel connection for some tests) for a sequence of different DUTs at the same measurement pin(s). Measurement time is typically a small fraction of the stress time and thus all measurements can be performed serially without affecting the total test time.

FIGS. 12-14 illustrate an embodiment of a packaged test chip 158 using a dual serial register to simultaneously subject different DUT arrays to two different stress conditions e.g. a hot carrier test and a PBTI test. The concept can be scaled up to three or more different stress conditions and may be implemented with a single serial register as well.

As shown in FIG. 12, there are now common sets of analog stress pins 160 and 162 but still one common set of analog measurement pins 164 and one common set of digital pins 166. The stress biasing resources on the benchtop tester are also doubled, i.e. the benchtop tester now has two stress utility plug-in daughter cards. Each daughter card is connected to only one set of analog pins on the test chip, i.e. the first set of stress and measurement utility plug-in cards are connected to the stress and measurement analog pins shown on the left side of the packaged chip and the second stress utility, plug-in card is connected to the stress analog pins shown on the top side of the package. In a similar manner the capability to perform three or more simultaneous tests with different stress conditions can be built into the system, the amount of package pins and utility daughter cards on the benchtop tester will increase.

FIG. 13 shows the changes needed on the register level to accommodate different tests that are executed in parallel. DUT register 170 does not change. Command register 172 needs additional sub-cells for stressing. These added sub-cells 174 are labeled as 'S2'. Analogously, a third additional sub-cell (S3) per DUT array would need to be added to the command register in order to have a capability for three parallel test with different stress conditions. It is assumed that there is no need to measure two or more DUT arrays simultaneously, the measurement being a relatively fast operation.

FIG. 14 shows the changes needed on the DUT level to accommodate different tests that are executed in parallel. Each switch block 176 now includes two stress switches STESS1 and STESS2 on every terminal of every DUT to have the capability to perform two different tests simultaneously on one test chip. Analogously, three tests would require three stress switches. No additional measurement switches are needed since there is no major benefit in measuring DUTs from two arrays simultaneously. A DUT control logic block 178 needs one additional input and output signal per added stress condition.

The degradation mechanisms can be accelerated considerably with high temperatures during testing. The higher the temperature the faster the degradation will be and the shorter the time needed for testing. These types of tests are normally done by placing the test samples in an oven or placing test wafers on a hot chuck. The maximum temperature is limited by the temperature rating of the package that can be as low as 150 C. The usefulness of these techniques is further limited by the fact that the actual temperatures inside the chips are not known, especially when the DUTs are biased, which causes additional local temperature increase on top of the oven temperature. Local polysilicon resistor heaters have been used on wafer level reliability testing. In these wafer level tests the DUTs have been heated individually, one at a time.

Figure 15:
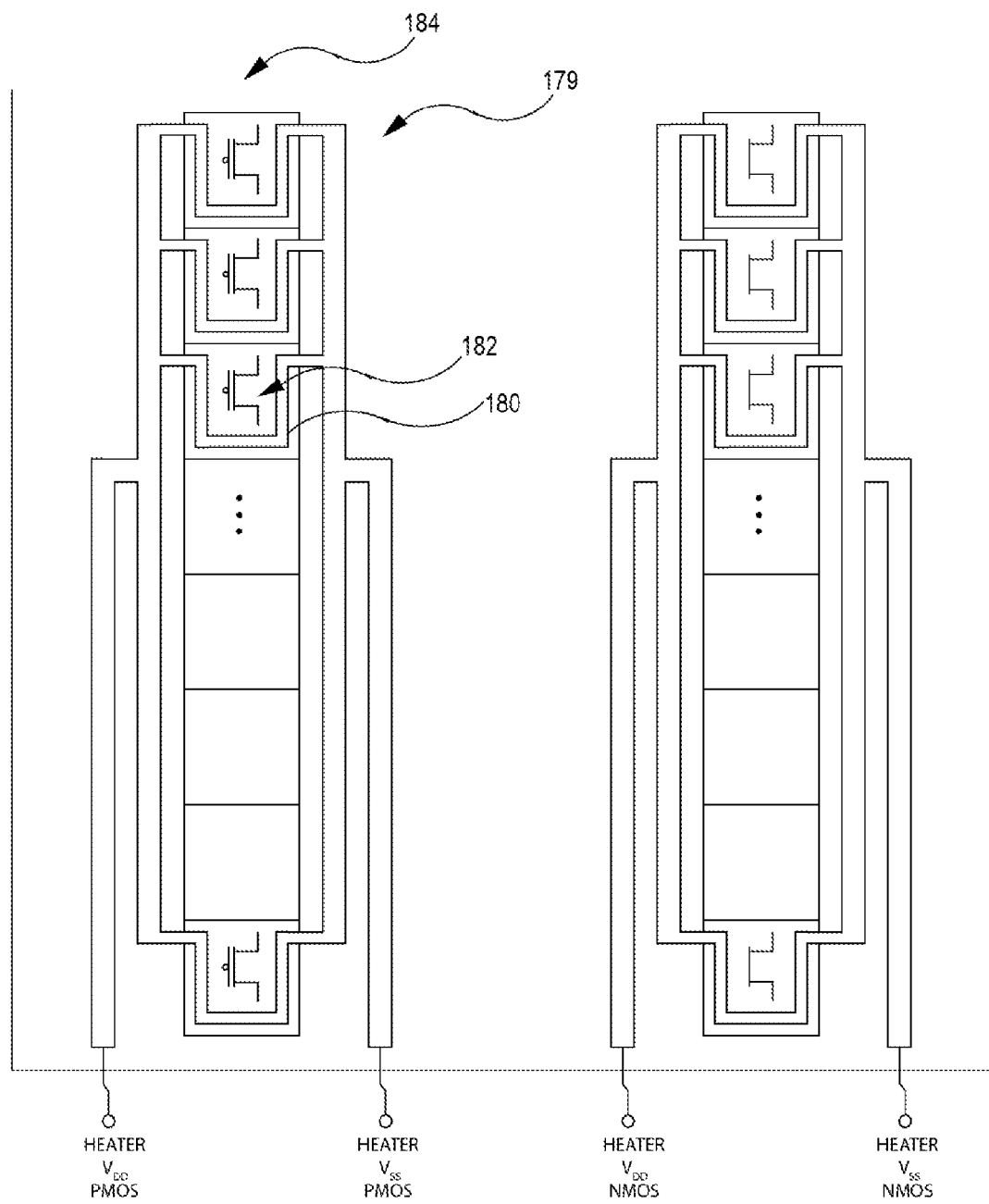
FIG. 15 is a diagram of die level heating elements around the IC test devices.

As shown in FIG. 15, arrays 179 of U-shaped local heaters 180 are wrapped around individual DUTs 182 in DUT arrays 184. The heaters are parallel connected similar to the corresponding DUT array, each heater array having its own heater VDD and VSS pins. The local heaters are resistive elements, such as poly resistors, polysilicon strips (e.g. formed from the gate polysilicon in a CMOS process) or diffusion resistors that are used to increase the temperature of the DUTs locally. The power to these heaters is delivered from the benchtop tester unit. Both DC current and pulse width modulated (PWM) heating can be used with the described heater to increase the temperature of the DUT to over 300 C.

The heaters cannot be addressed through switches because the overall resistance of the connections to and from a heater has to be kept low for maximum power transfer from electricity to heat in the vicinity of the DUT. The resistance of the actual resistive heaters wrapped around the DUT is kept at least hundred times higher than the combined resistance of the connections to the pins so that the heating power will be generated next to the DUT and not along the connections.

Temperature control is achieved by monitoring the temperature during the heating and feeding this information back to the benchtop tester, which sets the heating power in a way that the temperature stays constant at the desired value during the test period. Three techniques are used to monitor the temperature in this feedback control system: 1) using temperature measurement diodes placed as close to the DUTs as possible, 2) measuring the temperature from the DUT itself, e.g. from the changes in the drain current of a FET or the resistance of a via or 3) measuring the temperature from the resistance changes in the heaters. All these measurements can be performed with the benchtop tester.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

I claim:

1. A programmable test chip for characterization of an integrated circuit (IC) fabrication process, said test chip comprising:
   a die fabricated with said IC fabrication process;
   a plurality of contacts on the die including a first common set of addressing contacts configured to receive measurement selection commands and a second common set of measurement contacts;

a plurality of devices under test (DUT) on the die, said second common set of measurement contacts coupled to each DUT, each said DUI comprising a test device having one or more terminals and one or more switch blocks, each said switch block including a measurement switch coupled between one of the terminals and one of the measurement contacts in the second common set; and an addressing circuit on the die that couples the first common set of addressing contacts to each of the DUT switch blocks, said switch blocks responsive to said measurement selection commands to simultaneously test a plurality of DUTs and read out serially one or more measurement signals for the tested DUTs at the second common set of one or more of the measurement contacts to characterize the IC fabrication process.

2. The test chip of claim 1, wherein said measurement selection commands comprise digital measurement selection commands, wherein said plurality of DUTs are grouped into a plurality of equal length linear DUT arrays, said addressing circuit comprises a DUT serial register coupled to one of the addressing contacts to receive and store digital measurement selection commands for individual DUTs in the linear array in respective cells of the DUT serial register that are each connected to the same DUT in every linear array, and a command serial register coupled to another one of the addressing contacts to receive and store digital measurement selection commands for DUT arrays in respective cells of the command serial register that are each connected to all of the DUTs in the respective DUT arrays, each said DUT further comprising a logic block responsive to the measurement selection commands for individual DUTs and DUT arrays to control the one or more switch blocks.

3. The test chip of claim 1, wherein said die includes a third common set of stress contacts, each said switch block including a stress switch coupled between the terminal and one of the stress conta.cts, said addressing circuit responsive to the measurement selection commands to close the stress switches for a first group of DUTs to couple the addressing contacts in the third common set to the DUT terminal to apply first bias conditions to simultaneously stress the DUTs in the first group, said addressing circuit responsive to the measurement selection commands to open the stress switches and close the measurement switches for the first group of DUTs one DUT at a time to read out serially the one or more measurement signals.

4. The test chip of claim 3, wherein said die includes a fourth common set of stress contacts, each said switch block including a second stress switch coupled between the terminal and one of the stress contacts, said addressing circuit coupling the addressing contacts in the fourth common set to the DUT switch blocks to selectively apply second bias conditions to stress a second group of one or more DUTs while the first bias conditions are applied to stress the first group.

5. The test chip of claim 3, wherein said die is packaged as a packaged test chip with a plurality of external pins that are connected to respective addressing, stress and measurement contacts, wherein the number of DUTs on the die is greater than the number of external pins.

6. The test chip of claim 3, wherein said die is packaged in as a packaged test chip with a plurality of external pins that are connected to respective addressing, stress and measurement contacts, said DUTs grouped into arrays each including multiple DUTs, further comprising a plurality of resistive heating elements fabricated on the die and wrapped around the DUTs in the respective DUT arrays, each resistive element coupled to and through a pair of contacts on the die to a pair of external heat pins.

7. A method of characterizing an integrated circuit (IC) fabrication process comprising:

providing a test chip comprising a die fabricated with said IC fabrication process, a plurality of devices under test (DUT) on the die, a plurality of contacts on the die including a first common set of addressing contacts and a second common set of measurement contacts coupled to each said DUT, each said DUT comprising a test device having one or more terminals and one or more switch blocks, each said switch block including a measurement switch coupled between one of the terminals and one of the measurement contacts in the second common set, and an addressing circuit on the die that couples the first set of addressing contacts to each of the DUT switch blocks;

connecting off-chip analog current or voltage sources and analog current or voltage meters to one or more of the measurement contacts; and applying measurement selection commands for the plurality of DUTs to one or more addressing contacts to control the DUT switch blocks to simultaneously test a plurality of DUTs and read out serially one or more measurement signals for a the tested DUTs through the second common set of one or more of the measurement contacts to the current or voltage meters to characterize the IC fabrication process.

8. The method of claim 7, wherein said measurement selection commands coin rise a sequence of digital measurement selection commands, wherein said plurality of DUB are grouped into a plurality of equal length linear DUT arrays, said addressing circuit comprises a DUT serial register coupled to one of the addressing contacts to receive and store the digital measurement selection commands for individual DUTs in the linear array in respective cells of the DUI serial register that are each connected to the same DUT in every linear array, and a command serial register coupled to another one of the addressing contacts to receive and store the digital measurement selection commands for DUT arrays in respective cells of the command serial register that are each connected to all of the DUTs in the respective DUT arrays, each said DUT further comprising a logic block responsive to the measurement selection commands for individual DUTs and DUT arrays to control the one or more switch blocks.

9. The method of claim 7, Wherein each said switch block includes a second measurement switch coupled between the terminal and a different measurement contact, said second measurement switch switched with said measurement switch to measure a bias condition at the terminal to calibrate the measurement signal.

10. The method of claim 7, further comprising processing the one or more measurement signals for the tested DUTS to estimate a process variation for the IC fabrication process.

11. The method of claim 7, Wherein said die includes a third common set of stress contacts, each said switch block including a stress switch coupled between the terminal and one of the stress contacts, said addressing circuit coupling the addressing contacts in the third common set to the DUT switch blocks, further comprising:

connecting off-chip analog current or voltage sources to one or more of the stress contacts in the third common set; and applying stress selection commands with the measurement selection commands to control the DUT switch block stress switches to selectively apply first bias conditions to stress and degrade a first group of one or more test devices, wherein said addressing circuit o ens the stress switches and closes the measurement switches for one MIT at a time to read out seriall the one or more measurement signals for the stressed DUTs in the first group at the second common set of the one or more measurement contacts.

12. The method of claim 11, wherein the selection commands apply the first bias conditions to stress and degrade the first group of one or more devices over a time period and the measurement selection commands periodically measure each said DUT in the first group over the time period to pass the one or more measurement signals through the one or more of the measurement contacts as indicating a level of degradation of the DUTs.

13. The method of claim 12, wherein said die includes a fourth common set of stress contacts, each said switch block including a second stress switch coupled between the terminal and one of the stress contacts, said addressing circuit coupling the addressing contacts in the fourth common set to the DUT switch blocks, further comprising:

connecting off-chip analog current or voltage sources to one or more of the stress contacts in the fourth common set; and applying stress selection commands with the measurement selection commands to control the DUT switch block second stress switches to selectively apply second bias conditions to simultaneously stress and degrade a second group of one or more test devices, said measurement selection commands periodically measuring each said DUT in the first group and then the second group over the time period to pass the one or more measurement signals through the same one or more of the measurement contacts as indicating a level of degradation of the DUTs in the first group and then the second group.

14. The method of claim 11, wherein said die is packaged as a packaged test chip with a plurality of external pins that are connected to respective addressing, stress and measurement contacts, said DUTs grouped into arrays each including multiple DUTs, said die include a plurality of resistive heating elements fabricated on the die and wrapped around the DUTs in the respective DUT arrays, each resistive element coupled to through a pair of contacts on the die to a pair of external heat pins, further comprising:

applying power through the pair of external heat pins to the resistive heating element to locally heat the DUTs in the DUT array.

15. A system for characterization of an integrated circuit (IC) fabrication process, said system comprising:

a test chip comprising a die fabricated with said IC fabrication process, a plurality of devices under test (DUT) on the die, a plurality of contacts on the die including a first common set of addressing contacts and a second common set of measurement contacts coupled to each said DUT, each said DUT comprising a test device having one or more terminals and one or more switch blocks, each said switch block including a measurement switch coupled between one of the terminals and one of the measurement contacts in the second common set, and an addressing circuit on the die that couples the first set of addressing contacts to each of the DUT switch blocks;

a host controller configured to display a user interface for selection of test modes and specification of test conditions to define a test procedure and to display test data from the test procedure; and a bench top tester in communication with the host controller, said tester comprising programmable voltage and current stress sources, programmable voltage and current measurement sources, voltage and current meters, and an addressing circuit arranged in a universal interface, an adaptor having an input interface that mates with the universal interface and an output interface that mates with the common sets of contacts on the test chip, one or more controllers responsive to the selected test modes and specified test conditions to program the sources and to control the addressing circuit to apply a sequence of digital measurement selection commands for the plurality of DUTs to one or more addressing contacts to control the DUT switch blocks to simultaneously test a plurality of DUTs and read out serial one or more measurement signals for the tested DUTs through the second common set of one or more measurement contacts to the current or voltage meters to execute the test procedure, and an analog-to-digital converter (ADC) that digitizes the measurement signals from the voltage and current meters to produce digitized test data that is communicated to the host computer to characterize the IC fabrication process.

16. The system of claim 15, wherein said die includes a third common set of stress contacts connected to programmable voltage or current sources on the tester, each said switch block including a stress switch coupled between the terminal and one of the stress contacts, said addressing circuit coupling the addressing contacts in the third common set to the DUT switch blocks to selectively apply first bias conditions to stress a first group of one or more test devices, said addressing circuit configured to read out serially one or more measurement signals for the stressed DUTs through the second common se of one or more measurement contacts.

17. The system of claim 15, wherein said die is packaged into a packaged test chip with a plurality of external pins that are connected to respective addressing and measurement contacts, wherein said adapter comprises an interface card whose output interface mates with the external pins on the packaged test chip, wherein the number of DUTs on the die is greater than the number of external pins on the packaged test chip.

18. The system of claim 15, wherein execution of the test procedure on a single test chip characterizes process variation and degradation mechanisms of the IC fabrication process.

19. A programmable test chip for characterization of an integrated circuit (IC) fabrication process, said test chip comprising:

a die fabricated with said IC fabrication process;

a plurality of devices under test (DUT) on the die, each said DUT comprising a test device having one or more terminals and one or more switch blocks including stress and measurement switches with each said switch block coupled to one of the terminals, each said switch including a control terminal, a first terminal and second terminal connected to the respective device terminal;

one or more analog stress buses on the die that connect the first terminals of the stress switches together for the one or more terminals of each of the DUTs;

one or more analog measurement buses on the die that connect the first terminals of the measurement switches together for the one or more terminals of each of the DUTs;

a plurality of contacts on the die including a first common set of addressing contacts for receiving a sequence of digital stress and measurement selection commands for each of the plurality of DUTs, a second common set of stress contacts connected to the one or more analog stress buses to supply current or voltage signals to bias and stress the DUTs and a third common set of measurement contacts connected to the one or more analog measurement buses to both supply current or voltage signals to bias the DUTs for measurement and to provide access for current or voltage meters to one or more terminals of the DUT to measure one or more measurement signals; and an addressing circuit on the die, said addressing circuit comprising at least one serial register that stores the stress and measurement selection commands for each subsequent entry in the sequence and couples the selection commands to the control terminals of the stress and measurement switches to selectively and simultaneously stress a plurality of test devices and to read out serially one or more measurement signals for the stressed DUTs to the one or more of the measurement contacts to characterize the IC fabrication process.

* * * * *